(12) United States Patent
Hanes, II

(10) Patent No.: US 8,998,803 B2
(45) Date of Patent: Apr. 7, 2015

(54) DISSECTION AND RETRACTION DEVICE FOR VAGINAL SACRAL COLPOPEXY

(75) Inventor: Charles R. Hanes, II, Mobile, AL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 485 days.

(21) Appl. No.: 12/760,055

(22) Filed: Apr. 14, 2010

(65) Prior Publication Data

US 2010/0280627 A1  Nov. 4, 2010

Related U.S. Application Data

(60) Provisional application No. 61/214,960, filed on Apr. 30, 2009.

(51) Int. Cl.
| A61B 1/00 | (2006.01) |
| A61B 17/02 | (2006.01) |
| A61B 17/42 | (2006.01) |
| A61B 17/34 | (2006.01) |
| A61F 2/00 | (2006.01) |

(52) U.S. Cl.
CPC .............. *A61B 17/0218* (2013.01); *A61B 17/42* (2013.01); *A61B 17/0206* (2013.01); *A61B 17/3462* (2013.01); *A61F 2/0045* (2013.01)

(58) Field of Classification Search
CPC ........... A61B 17/0206; A61B 17/0218; A61B 17/3462; A61B 17/42; A61M 29/00; A61F 2/0045
USPC ................. 606/119, 190–191, 193, 197–199; 600/204, 206, 210, 215, 220–223, 245, 600/184, 187, 190, 193, 196, 197
See application file for complete search history.

(56) References Cited

U.S. PATENT DOCUMENTS

| 1,222,478 | A | * | 4/1917 | Sheaff ........................... 600/220 |
| 5,209,754 | A | | 5/1993 | Ahluwalia |
| 5,304,187 | A | | 4/1994 | Green et al. |
| 5,354,292 | A | | 10/1994 | Braeuer et al. |

(Continued)

FOREIGN PATENT DOCUMENTS

| DE | 4115548 A1 | 11/1991 |
| WO | 96/27332 A1 | 9/1996 |

(Continued)

OTHER PUBLICATIONS www.thefreedictionary.com/unitary, definition of hte term unitary retrieved Apr. 2, 2014.*

(Continued)

*Primary Examiner* — David Eastwood
(74) *Attorney, Agent, or Firm* — Brake Hughes Bellermann LLP

(57) ABSTRACT

In one embodiment the apparatus includes a first retractor, a second retractor, and a shaft. The shaft defines a central channel extending from a first end portion of the shaft to a second end portion of the shaft. The first retractor and the second retractor are configured to collectively form a lumen. The shaft is configured to be disposed within the lumen. In one embodiment method of disposing a graft within a body of a patient, includes making an incision in the body of the patient, inserting a medical device into the body of the patient through the incision, removing the shaft of the medical device from the body of the patient, and moving the first refractor within the body of the patient away from the second retractor.

16 Claims, 2 Drawing Sheets

(56) References Cited

U.S. PATENT DOCUMENTS

| | | | |
|---|---|---|---|
| 5,843,108 A * | 12/1998 | Samuels | 606/167 |
| 5,976,146 A * | 11/1999 | Ogawa et al. | 606/86 R |
| 6,126,594 A * | 10/2000 | Bayer | 600/184 |
| 6,235,037 B1 | 5/2001 | East et al. | |
| 6,315,713 B1 * | 11/2001 | Takada | 600/114 |
| 6,319,272 B1 | 11/2001 | Brenneman et al. | |
| 6,364,832 B1 * | 4/2002 | Propp | 600/220 |
| 6,423,075 B1 | 7/2002 | Singh et al. | |
| 6,572,631 B1 | 6/2003 | McCartney | |
| 6,592,515 B2 | 7/2003 | Thierfelder et al. | |
| 6,712,795 B1 | 3/2004 | Cohen | |
| 6,755,781 B2 | 6/2004 | Gellman | |
| 6,884,212 B2 | 4/2005 | Thierfelder et al. | |
| 6,936,052 B2 | 8/2005 | Gellman et al. | |
| 6,953,428 B2 | 10/2005 | Gellman et al. | |
| 6,991,597 B2 | 1/2006 | Gellman et al. | |
| 7,025,063 B2 | 4/2006 | Snitkin et al. | |
| 7,025,772 B2 | 4/2006 | Gellman et al. | |
| 7,070,558 B2 | 7/2006 | Gellman et al. | |
| 7,235,043 B2 | 6/2007 | Gellman et al. | |
| 7,867,222 B1 | 1/2011 | Tilton, Jr. et al. | |
| 7,874,982 B2 * | 1/2011 | Selover et al. | 600/245 |
| 8,454,644 B2 * | 6/2013 | McDonnell | 606/190 |
| 8,734,319 B2 | 5/2014 | Hanes | |
| 2002/0028980 A1 | 3/2002 | Thierfelder et al. | |
| 2002/0123668 A1 * | 9/2002 | Ritland | 600/210 |
| 2003/0236447 A1 * | 12/2003 | Ritland | 600/210 |
| 2004/0093001 A1 * | 5/2004 | Hamada | 606/190 |
| 2004/0230092 A1 | 11/2004 | Thierfelder et al. | |
| 2005/0038462 A1 | 2/2005 | Lubock et al. | |
| 2005/0065395 A1 | 3/2005 | Mellier | |
| 2005/0107805 A1 | 5/2005 | Bouffier et al. | |
| 2005/0216013 A1 * | 9/2005 | Dallara et al. | 606/72 |
| 2006/0173483 A1 | 8/2006 | Kieturakis et al. | |
| 2006/0212046 A1 * | 9/2006 | Pearce et al. | 606/140 |
| 2006/0229656 A1 * | 10/2006 | McDonnell | 606/191 |
| 2006/0260618 A1 | 11/2006 | Hodroff et al. | |
| 2007/0219416 A1 * | 9/2007 | Perez-Cruet et al. | 600/219 |
| 2008/0207988 A1 | 8/2008 | Hanes | |
| 2008/0275306 A1 * | 11/2008 | Rebuffat et al. | 600/184 |
| 2009/0005646 A1 * | 1/2009 | Nowitzke et al. | 600/187 |
| 2009/0099422 A1 * | 4/2009 | George | 600/214 |
| 2011/0208226 A1 * | 8/2011 | Fatone et al. | 606/191 |

FOREIGN PATENT DOCUMENTS

| | | |
|---|---|---|
| WO | 02/19946 A2 | 3/2002 |
| WO | 02/098301 A1 | 12/2002 |
| WO | 2005/110273 A1 | 11/2005 |

OTHER PUBLICATIONS www.thefreedictionary.com/Cannulate, definition of the term cannulated, retrieved Apr. 1, 2014.*

Barber, et al., "Bilateral Uterosacral Ligament Vaginal Vault Suspension With Site-Specific Endopelvic Fascia Defect Repair for Treatment of Pelvic Organ Prolapse", American Journal of Obstetric Gynecology, vol. 183, No. 6, Dec. 2000, pp. 1402-1411.

Benson, et al., "Vaginal Versus Abdominal Recontructive Surgery for the Treatment of Pelvic Support Defects: A Prospective Randomized Study with Long-Term Outcome Evaluation", American Journal of Obstetric Gynecology, vol. 175, Dec. 1996, pp. 1418-1422.

Cundiff, et al., "Abdominal Sacral Colpoperineopexy: A New Approach for Correction of Posterior Compartment Defects and Perineal Descent Associated with Vaginal Vault Prolapse", American Journal of Obstetric Gynecology, vol. 177, No. 6, Dec. 1997, pp. 1345-1355.

Elliott, et al., "Long-Term Results of Robotic Assisted Laparoscopic Sacrocolpopexy for the Treatment of High Grade Vaginal Vault Prolapse", Journal of Urology, vol. 176, No. 2, Aug. 2006, pp. 655-659.

Karram, et al., "High Uterosacral Vaginal Vault Suspension with Fascial Reconstruction for Vaginal Repair of Enterocele and Vaginal Vault Prolapse", American Journal of Obstetric Gynecology, vol. 185, No. 6, Dec. 2001 , pp. 1339-1343.

Maher, et al., "Abdominal Sacral Colpopexy or Vaginal Sacrospinous Colpopexy for Vaginal Vault Prolapse: A Prospective Randomized Study", American Journal of Obstetric Gynecology, vol. 190, No. 1, Jan. 2004, pp. 20-26.

Morley, et al., "Sacrospinous Ligament Fixation for Eversion of the Vagina", American Journal of Obstetric Gynecology, vol. 158, No. 5, Apr. 1988, pp. 872-881.

Nezhat, et al., "Robotic-Assisted Laparoscopy in Gynecological Surgery", Scientific Paper, Journal of the Society of Laparoendoscopic Surgeons, vol. 10, No. 3, 2006, pp. 317-320.

Nygaard, et al., "Abdominal Sacrocolpopexy: A Comprehensive Review", Obstetrics & Gynecology, vol. 104, No. 4, Oct. 2004, pp. 805-823.

Ross, Jim W., "Techniques of Laparoscopic Repair of Total Vault Eversion After Hysterectomy", Journal of the American Association of Gynecological Laparoscopy, vol. 4, No. 2, Feb. 1997, pp. 173-183.

Shull, et al., "A Transvaginal Approach to Repair of Apical and Other Associated Sites of Pelvic Organ Prolapse with Uterosacral Ligaments", American Journal of Obstetric Gynecology, vol. 183, No. 6, Dec. 2000, pp. 1365-1374.

Silva, et al., "Uterosacral Ligament Vault Suspension: Five-Year Outcomes", Obstetrics & Gynecology, vol. 108, No. 2, Aug. 2006 pp. 255-263.

Su, et al., "Abdominovaginal Sacral Colpoperineopexy: A Quality of Life Assessment", Journal of Pelvic Medicine & Surgery, vol. 13, No. 4, Jul./Aug. 2007, pp. 181-190.

Sze, et al., "Transvaginal Repair of Vault Prolapse: A Review", Obstetrics & Gynecology, vol. 89, No. 3, Mar. 1997, pp. 466-475.

Van Der Weiden, R. M. F., et al., "A New Device for Bone Anchor Fixation in Laparoscopic Sacrocolpopexy: The Franciscan Laparoscopic Bone Anchor Inserter", Surgical Endoscopy and Other Interventional Techniques, vol. 19, No. 4, Apr. 2005, pp. 594-597.

Visco, et al., "Vaginal Mesh Erosion After Abdominal Sacral Colpopexy", American Journal of Obstetric Gynecology, vol. 184, Feb. 2001 ,pp. 297-302.

Medcompare, "Prolene and Mersilene, Description of Products: Polyethylene Mesh Prolene and Polyester Mesh Mersilene, Medcompare—The Buyer's Guide for Medical Professionals", document available at: http://www.medcompare.com/details/358621/prolene-polypropylene, Jun. 25, 2008.

"ProTrak 5 mm (Single Use Instrument), Description of product: ProTrak 5 mm (Single Use Instrument), Autosuture—Advancing Possibilities in Surgery", document available at: http:www.autosuture.com, Jun. 25, 2008.

Hall, et al., "Laparoscopic Sacrocolpopexy: Lessons Learned", Journal of Pelvic Medicine and Surgery, vol. 13, No. 4, Jul./Aug. 2007, pp. 197-201.

Flynn, et al., "Abdominal Surgery for Pelvic Organ Prolapse", Journal of Pelvic Medicine & Surgery, vol. 13, No. 4, Jul./Aug. 2007, pp. 157-170.

International Search Report and Written Opinion for International Application No. PCT/US2010/031271, mailed Jul. 2, 2010, 16 pages.

Final Office Action for U.S. Appl. No. 12/039,488, mailed Apr. 6, 2012, 19 pages.

Non-Final Office Action for U.S. Appl. No. 12/039,488, mailed Nov. 9, 2011, 15 pages.

Final Office Action Response for U.S. Appl. No. 12/039,488, filed Jun. 5, 2012, 11 pages.

Non-Final Office Action Response for U.S. Appl. No. 12/039,488, filed Feb. 8, 2012, 10 pages.

First Examiner's Report for Australian Application No. 2008221334, mailed Jul. 19, 2012, 3 pages.

Notice of Allowance for U.S. Appl. No. 12/039,488, mailed Jan. 15, 2014, 9 pages.

Office Action for CA Application No. 2,679,392, mailed May 27, 2014, 2 pages.

* cited by examiner

DISSECTION AND RETRACTION DEVICE FOR VAGINAL SACRAL COLPOPEXY

CROSS REFERENCE TO RELATED APPLICATIONS

This application is a nonprovisional of, and claims priority to, U.S. Patent Application No. 61/214,960, filed Apr. 30, 2009, entitled "DISSECTION AND RETRACTION DEVICE FOR VAGINAL SACRAL COLPOPEXY," and is related to U.S. patent application Ser. No. 12/039,488, both of which are incorporated by reference herein.

BACKGROUND

This invention enables a sacral colpopexy operation to be performed by means of vaginal surgery. Traditionally, this operation has been performed through an abdominal incision.

The abdominal sacral colpopexy (ASC) is widely recognized as the "gold standard" of all operations for the correction of vaginal vault prolapse. However, there are a large number of surgeons that advocate vaginal surgery using surgical procedures and devices that suspend the vagina to the uterosacral or sacrospinous ligaments. They point to studies showing that vaginal surgery~in general, is easier for the patient to recover from and often has lower operative morbidity than the abdominal operations.

Clinical studies comparing ASC with the vaginal procedures have indicated greater success with the ASC and a lower failure rate, but the ASC does carry a higher complication rate.

If the sacral colpopexy operation can be performed using a vaginal technique that does not deviate from the optimal abdominal technique, then the advantages of being able to offer the gold standard operation will be enhanced by avoiding those aspects of abdominal surgery that are unattractive both to surgeons and patients. In addition, if this can be done in a fashion that is technically safe and easy, it is anticipated that many surgeons would incorporate this into their standard practice.

One of the technical challenges of the sacral colpopexy is to avoid the middle sacral vessels when fixing the graft to the presacral fascia. This instrument enables visualization of these vessels thereby providing the ability to fix the graft at a safe distance from the vessels.

This instrument is a modification of the instrument previously filed (U.S. patent application Ser. No. 12/039,488). This modification results in the sleeve used to house the dissecting instrument being in two pieces rather than one. These two pieces, when approximated, from the channel through which the dissecting instrument slides. When the dissecting instrument is removed, the two pieces are then used as retractors enabling direct visualization of the operative field. The distal ends of these retractors would be in close proximity to the sacrum and would expose the presacral fascial sheath so that the graft material could then be fixed to this fascial sheath under direct visualization. The use of these retractors takes the place of the operating instrument described in U.S. patent application Ser. No. 12/039,488.

SUMMARY

The invention enables the operating surgeon to create a tunnel from the vaginal apex to the sacrum while remaining in the retroperitoneal space and to identify the middle sacral vessels before fixation of the graft material to the sacrum or presacral fascia. The graft may then be safely fixed using sutures, helical tacks or bone anchors.

This provides the patient with certain distinct advantages. She is able to have the "gold standard" operation using a vaginal technique that does not deviate from the accepted, optimal abdominal technique in any way other than the approach to the operative site. She, therefore, may benefit from the advantages of vaginal surgery as compared with abdominal surgery, quicker recovery and less surgical morbidity.

This invention also provides the surgeon with distinct advantages. He/she is able to offer the patient a surgical repair that is the "gold standard" and can be done quicker than the ASC.

Another advantage is that with this vaginal approach, the posterior compartment can be repaired through the same incision. By contrast, in the ASC procedure, if a posterior compartment defect exists, the surgeon would normally have to make a separate vaginal incision after completing the ASC to perform the repair.

DETAILED DESCRIPTION

Figure 1:
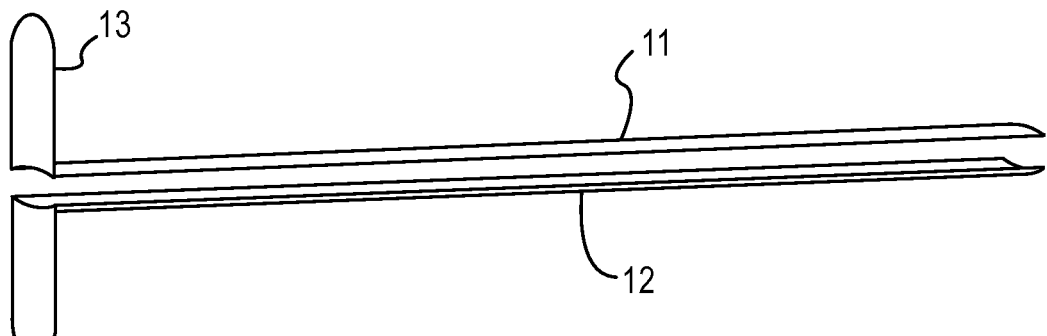
FIG. 1 is a perspective view from the user's right side of the retraction device.
Figure 2:
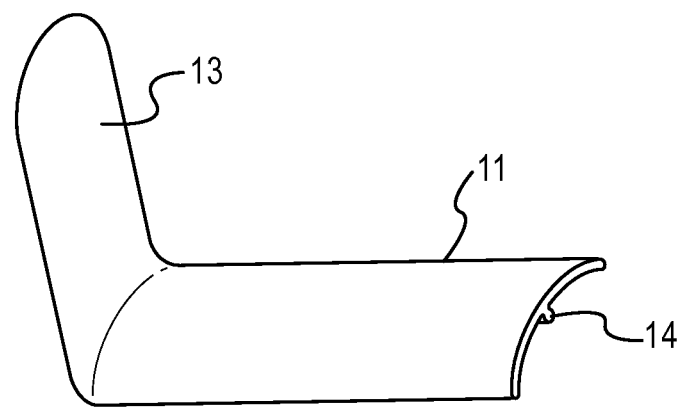
FIG. 2 is another view of one blade of the retraction device.

FIGS. 1 and 2 are perspective views from the user's right side of the retraction devices. The anterior blade 11 and the posterior blade 12 have handles 13. There may be a ridge 14 running down the midline of the inner surface of the blades. In one embodiment, the blades are long enough to reach from the vaginal opening to the sacral promontory.

Figure 3:
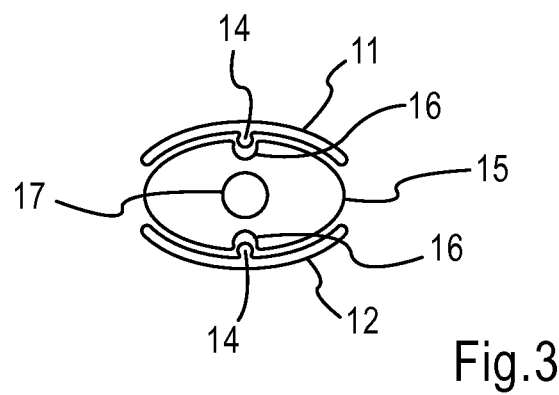
FIG. 3 is a perspective cross-sectional of the dissecting instrument and the retraction blades.

FIG. 3 shows the blades 11, 12 and the dissecting device 15. Note that the curvature of the blades is identical with the curvature on the anterior and posterior surfaces of the dissecting instrument. The blades may have a ridge on their inner surface 14 which slide into a corresponding groove 16 on the anterior and posterior surfaces of the dissecting instrument 15. This ridge and groove system enables the blades and the dissecting device to be inserted as one piece without separation. The central channel 17 in the dissection device allows for the insertion of a separate suction/irrigation instrument that is utilized for the creation of the tunnel in the soft tissue by hydrodissection as would be the case if a space were being created between the apex of the vagina and the sacrum.

Figure 4:
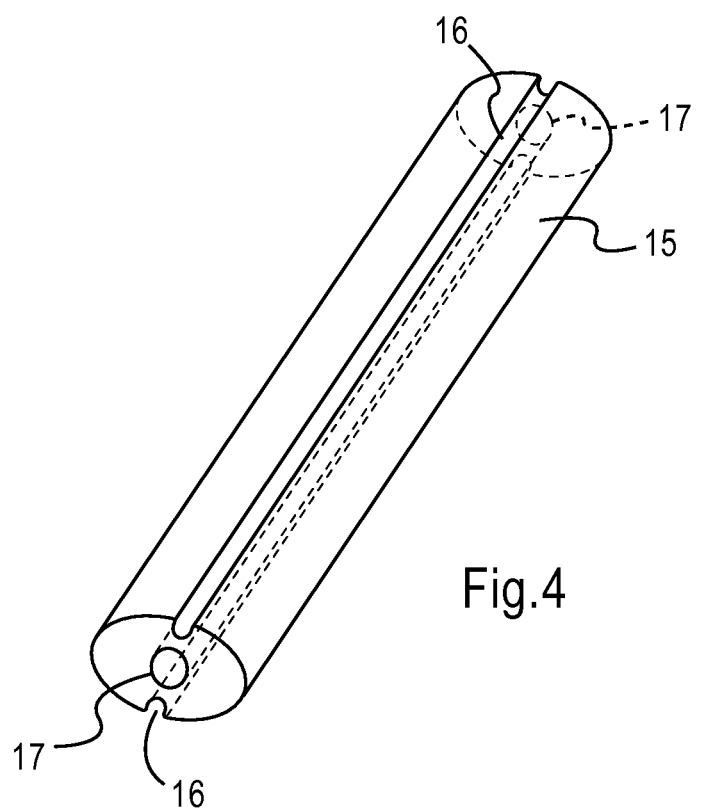
FIG. 4 is a perspective view from the user's right side of the dissection instrument.

FIG. 4 is a perspective views from the user's right side of the dissecting instrument 15. This instrument may be elliptical, circular or any combination of these shapes. Grooves 16 are seen on the anterior and the posterior surfaces. The central channel 17 traverses the full length of the instrument.

REFERENCE NUMERALS

11—Anterior blade
12—Posterior blade
13—Handle
14—Ridge on inner surface of blade
15—Dissecting instrument 16—Groove on dissecting instrument
17—Central channel of dissecting instrument

OPERATION

Prior to using the instrument, an incision will have been made in the vagina. The length of this incision is sufficient to accommodate the cross-sectional area of the instrument. Usually, this incision would be in the posterior vaginal wall although the anterior wall could also be used. The perirectal space between the rectum and vagina is developed usually with the aid of hydrodissection. This space is created up to the level of the vaginal apex and out laterally to the right pelvic sidewall.

The retractor blades 11, 12 are articulated to the dissecting instrument 15 by sliding the ridges 14 of the blades into the grooves 16 of the dissecting instrument. The end of the instrument is then inserted into the incision. Using hydrodissection through the central channel 17 of the dissecting instrument, a space is created between the vaginal apex and the sacrum. The instrument is advanced progressively to the sacrum as this space is created.

When the sacral promontory is reached, the dissecting instrument 15 is withdrawn by sliding it back out of the vagina leaving the retractor blades 11, 12 in place. The operating surgeon may then grasp the handles 13 of the blades and retract the blades in opposite directions from one another thereby exposing a larger area in front of the sacrum. With adequate direct lighting between the blades, this presacral space can be visualized. The tissue overlying the presacral fascia can be dissected off of the surface of the fascia using routine surgical techniques. The middle sacral vessels are identified so that a piece of graft material can be safely attached to the presacral fascia without causing significant bleeding.

When this fixation has been accomplished to the satisfaction of the operating surgeon~the retractor blades 11, 12 are withdrawn. Upon complete removal of the instrument~the graft remains in the operative field. One end is fixed to the sacrum while the other extends out of the vaginal incision. The remaining part of the sacral colpopexy procedure is completed by trimming the length of the graft and fixing it to the outer surfaces of the vagina using standard techniques.

Another incision may be made in the anterior vagina and a space created between the bladder and vagina as far as the vaginal apex. The two incisions may be joined around the apex. A piece of graft material may then be attached to the previously positioned piece and then attached to the outer surface of the anterior vagina, again using standard suture techniques.

OTHER VARIATIONS

The groove and ridge system that enables the retractor blades to be attached to the dissecting instrument is only one way to accomplish this articulation of the blades to the instrument. Any number of other modes of attachment could be used with the objective being to be able to insert the combination of the dissecting instrument and retractor blades as one piece. Disarticulation and withdrawal of the dissecting instrument from the blades then enables visualization of the presacral space and completion of the procedure.

Although, the operation described here is a sacral colpopexy, this instrument can also be used for a rectopexy in female patients as well as any other procedure requiring tunneling through soft tissue and direct visualization of the operative site.

What is claimed is:

1. An apparatus, comprising:
a first retractor having a handle portion and a blade portion, the handle portion extending from the blade portion in a direction different than a longitudinal axis of the blade portion of the first retractor, the blade portion of the first retractor having an inner surface, the inner surface of the blade portion of the first retractor including a first ridge protruding from the inner surface and spaced apart from lateral edges of the blade portion of the first retractor;
a second retractor having a handle portion and a blade portion, the handle portion extending from the blade portion in a direction different than a longitudinal axis of the blade portion of the second retractor, the blade portion of the second retractor having an inner surface, the inner surface of the blade portion of the second retractor including a second ridge protruding from the inner surface and spaced apart from lateral edges of the blade portion of the second retractor;
a shaft defining a central channel extending from a first end portion of the shaft to a second end portion of the shaft, the shaft having an outer surface defining a first groove and a second groove, the central channel being disposed between the first groove and the second groove,
the inner surface of the first retractor and the inner surface of the second retractor are configured to collectively form a lumen, the shaft being configured to be disposed between the first retractor and the second retractor, the first ridge of the first retractor configured to engage the first groove of the shaft, the second ridge of the second retractor configured to engage the second groove of the shaft, the handle portion of the first refractor and the handle portion of the second retractor extending away from each other and extending away from the shaft, the first retractor being configured to move with respect to the second retractor in a direction away from the second retractor.

2. The apparatus of claim 1, wherein the first groove and the second groove do not extend into the central channel.

3. The apparatus of claim 1, wherein the first groove is disposed on a first side of the outer surface of the shaft, and the second groove is disposed on a second side of the outer surface of the shaft, the first side being opposite to the second side, the first and second grooves extending along an entire length of the shaft.

4. The apparatus of claim 1, wherein the shaft is configured to be slidably disposed within the lumen.

5. The apparatus of claim 1, wherein the central channel is configured to receive an irrigation device.

6. The apparatus of claim 1, wherein the central channel is configured to receive a suction device.

7. The apparatus of claim 1, wherein the shaft has an elliptical cross-section.

8. The apparatus of claim 1, wherein the length of the lumen formed by the first retractor and the second retractor extends the entire length of the first refractor.

9. An apparatus, comprising:
a first retractor having a first ridge protruding from an inner surface of the first retractor and spaced apart from lateral edges of the first retractor;
a second retractor having a second ridge protruding from an inner surface of the second retractor and spaced apart from lateral edges of the second retractor;
a shaft having a tubular structure that defines a central channel extending through a body of the tubular structure from a first end portion of the shaft to a second end portion of the shaft, the shaft defining first and second grooves extending an entire length of the shaft, the central channel being disposed between the first groove and the second groove, the first groove being configured to slidably engage the first ridge of the first retractor, the second groove being configured to slidably engage the second ridge of the second retractor, the first retractor and the second retractor are configured to collectively form a lumen, the shaft being configured to be disposed within the lumen such that the first and second grooves defined by the shaft engages the first ridge of the first retractor and the second ridge of the second retractor, respectively.

10. The apparatus of claim 9, wherein the shaft is configured to be slidably disposed within the lumen.

11. The apparatus of claim 9, wherein the central channel is configured to receive an irrigation device.

12. The apparatus of claim 9, wherein the central channel is configured to receive a suction device.

13. The apparatus of claim 9, wherein the first retractor is configured to be moved away from the second retractor.

14. An apparatus, comprising:
a first retractor having a first ridge protruding from an inner surface of the first retractor and spaced apart from lateral edges of the first retractor;
a second retractor having a second ridge protruding from an inner surface of the second retractor and spaced apart from lateral edges of the second retractor;
a shaft having a tubular structure that defines a length extending from a first end of the shaft to a second end of the shaft, the shaft defining a central channel extending through a body of the tubular structure from the first end of the shaft to the second end of the shaft, the shaft defining first and second grooves extending the length of the shaft, the central channel being disposed between the first groove and the second groove, wherein the first ridge and the second ridge do not extend into the central channel, the first retractor and the second retractor are configured to collectively form a lumen, the shaft being configured to be disposed within the lumen.

15. The apparatus of claim 14, wherein the first groove is disposed on a first side of the outer surface of the shaft, and the second groove is disposed on a second side of the outer surface of the shaft, the first side being opposite to the second side, the first and second grooves extending along an entire length of the shaft.

16. The apparatus of claim 14, wherein the first retractor includes a curved inner surface having the first ridge, the second retractor includes a curved inner surface having the second ridge, the lumen being disposed between the inner surface of the first refractor and the inner surface of the second retractor.

* * * * *